(12) United States Patent
Murakami et al.

(10) Patent No.: US 8,025,630 B2
(45) Date of Patent: Sep. 27, 2011

(54) TREATMENT APPARATUS

(75) Inventors: Eiji Murakami, Hachioji (JP); Masaru Imoto, Machida (JP)

(73) Assignee: Olympus Medical Systems Corp. (JP)

( * ) Notice: Subject to any disclaimer, the term of this patent is extended or adjusted under 35 U.S.C. 154(b) by 637 days.

(21) Appl. No.: 11/359,533

(22) Filed: Feb. 22, 2006

(65) Prior Publication Data

US 2007/0239185 A1    Oct. 11, 2007

(51) Int. Cl.
*A61H 1/00* (2006.01)
(52) U.S. Cl. ............... 601/2; 606/169; 606/205; 604/22
(58) Field of Classification Search ................. 606/37, 606/169
See application file for complete search history.

(56) References Cited

U.S. PATENT DOCUMENTS

| | | | |
|---|---|---|---|
| 5,322,055 A * | 6/1994 | Davison et al. .................... 601/2 |
| 6,340,352 B1 * | 1/2002 | Okada et al. ....................... 601/2 |
| 6,423,082 B1 * | 7/2002 | Houser et al. .................. 606/169 |
| 6,432,118 B1 * | 8/2002 | Messerly ...................... 606/169 |

FOREIGN PATENT DOCUMENTS

JP    2002-078714    3/2002

* cited by examiner

*Primary Examiner* — Unsu Jung
*Assistant Examiner* — Nigel Fontenot
(74) *Attorney, Agent, or Firm* — Ostrolenk Faber LLP

(57) ABSTRACT

A treating device according to the present invention comprises: a transmitting member for transmitting energy, for treating living body tissue, to the living body tissue; an outer sheath through which the transmitting member is passed; and a grasping section supported at the tip end portion of the outer sheath so as to be capable of turning with respect to the transmitting member, which allows the living body tissue to be grasped against the transmitting member. With such an arrangement, curved portions are formed on each of the transmitting member and the grasping section such that the transmitting member and the grasping section are in close contact. Furthermore, an edge portion is provided to a tip end portion of the transmitting member, at the side of the transmitting member in the direction toward which the grasping section heads, at the time of the grasping section turning on the turning axis toward the transmitting member so as to close.

5 Claims, 12 Drawing Sheets

TREATMENT APPARATUS

BACKGROUND OF THE INVENTION

1. Field of the Invention

The present invention relates to a treating device, and more particularly relates to a treating device wherein living body tissue is grasped between an ultrasonic probe and a jaw, and the living body tissue is subjected to treatment such as incision, excision, coagulation, dissection, or the like.

2. Description of the Related Art

As of recent years, procedures have come to be performed wherein a slender endoscope is inserted into the body cavity so as to observe organs within the body cavity, and perform various types of medical treatment under endoscope observation as necessary.

One known method of the aforementioned medical treatment performed under endoscope observation is to perform medical treatment using a treating device. In the event that such a treating device uses ultrasonic waves for example as the energy for subjecting the living organism to treatment, the treating device is configured as an ultrasonic treating device, and is configured so as to enable treatment such as incision, excision, coagulation, or the like, by the living body tissue being grasped between an ultrasonic probe and a jaw.

Generally, such an ultrasonic treating device has a configuration in which an operator-side operating unit is connected to the base end portion of an outer sheath of an insertion portion, with an ultrasonic transducer for generating ultrasonic vibrations being disposed at this operating unit and a treating section for treating the living body tissue being disposed on the tip portion of the outer sheath of the insertion portion.

Also, a vibration transmitting member which is an ultrasonic probe for transmitting ultrasonic vibrations from the ultrasonic transducer to the treating section side is inserted through the interior of the outer sheath of the insertion portion. The base end portion of the vibration transmitting member is connected to the ultrasonic transducer. Further, a jaw is disposed on the treating section so as to be turnable as to the ultrasonic probe (vibration transmitting member).

Also, an operating handle for performing opening/closing operations of the jaw as to the ultrasonic probe is provided to the operating unit. Further, a jaw operating rod is inserted through the interior of the outer sheath of the insertion portion so as to be capable of advancing/retracting in the axial direction. The operating rod advances/retracts in the axial direction in accordance with the operations of the operating handle, so that the jaw of the treating section performs opening/closing operations as to the ultrasonic probe in accordance with the advancing/retracting actions of the operating rod. Such an arrangement enables the living body tissue to be grasped between the ultrasonic probe and the jaw by performing the closing operation of the jaw.

Next, the ultrasonic treating device transmits ultrasonic vibrations from the ultrasonic transducer to the treating section side via the vibration transmitting member, with the living body tissue thus grasped, thereby performing treatment such as incision, excision, coagulation, or the like, of tissue or blood vessels or the like while coagulating the living body tissue so as to prevent hemorrhaging due to frictional heat from mechanical vibrations.

Also, the reverse face from the grasping face on the tip side of the ultrasonic probe may be used with the ultrasonic treating device, so as to perform dissection treatment of living body tissue, such as dissecting the gallbladder from the liver.

A greater number of proposals have been made with such ultrasonic treating device with respect to conventional devices, in order to perform treatment such as incision, excision, coagulation, dissection, etc., of living body tissue, more efficiently.

For example, Japanese Unexamined Patent Application Publication No. 2002-78714 discloses art relating to ultrasonic treating devices wherein, in addition to performing coagulation and incision of living body tissue while grasping the living body tissue between a treating section of a vibration transmission member which is an ultrasonic probe and a grasping section of a jaw, a spatula-shaped portion is provided on the tip end of the ultrasonic probe so as to facilitate dissection processing of living body tissue with the spatula-shaped portion.

Also, U.S. Pat. No. 6,432,118 B1 discloses art relating to ultrasonic treating devices wherein a tip portion is formed in a non-symmetrical curved shape as to the plane of turning direction of a jaw, and further, an edge portion is provided in the generally axial direction on a face of a vibration transmitting member which is an ultrasonic probe, opposite to a grasping face where living body tissue is grasped, thereby enabling dissecting processing in addition to performing incision, excision, and coagulation of living body tissue.

SUMMARY OF THE INVENTION

Briefly, the treating device according to the present invention comprises: a transmitting member for transmitting energy, for treating living body tissue, to the living body tissue; an outer sheath through which the transmitting member is passed; and a grasping section supported at the tip end portion of the outer sheath so as to be capable of turning with respect to the transmitting member, which allows the living body tissue to be grasped against the transmitting member. With such an arrangement, curved portions are formed on each of the transmitting member and the grasping section such that the transmitting member and the grasping section are in close contact. Furthermore, an edge portion is provided to a tip end portion of the transmitting member, at the side of the transmitting member in the direction toward which the grasping section heads, at the time of the grasping section turning on the turning axis toward the transmitting member so as to close.

DETAILED DESCRIPTION OF THE PREFERRED EMBODIMENTS

Embodiments of the present invention will be described with reference to the drawings.

First Embodiment

Figure 1:
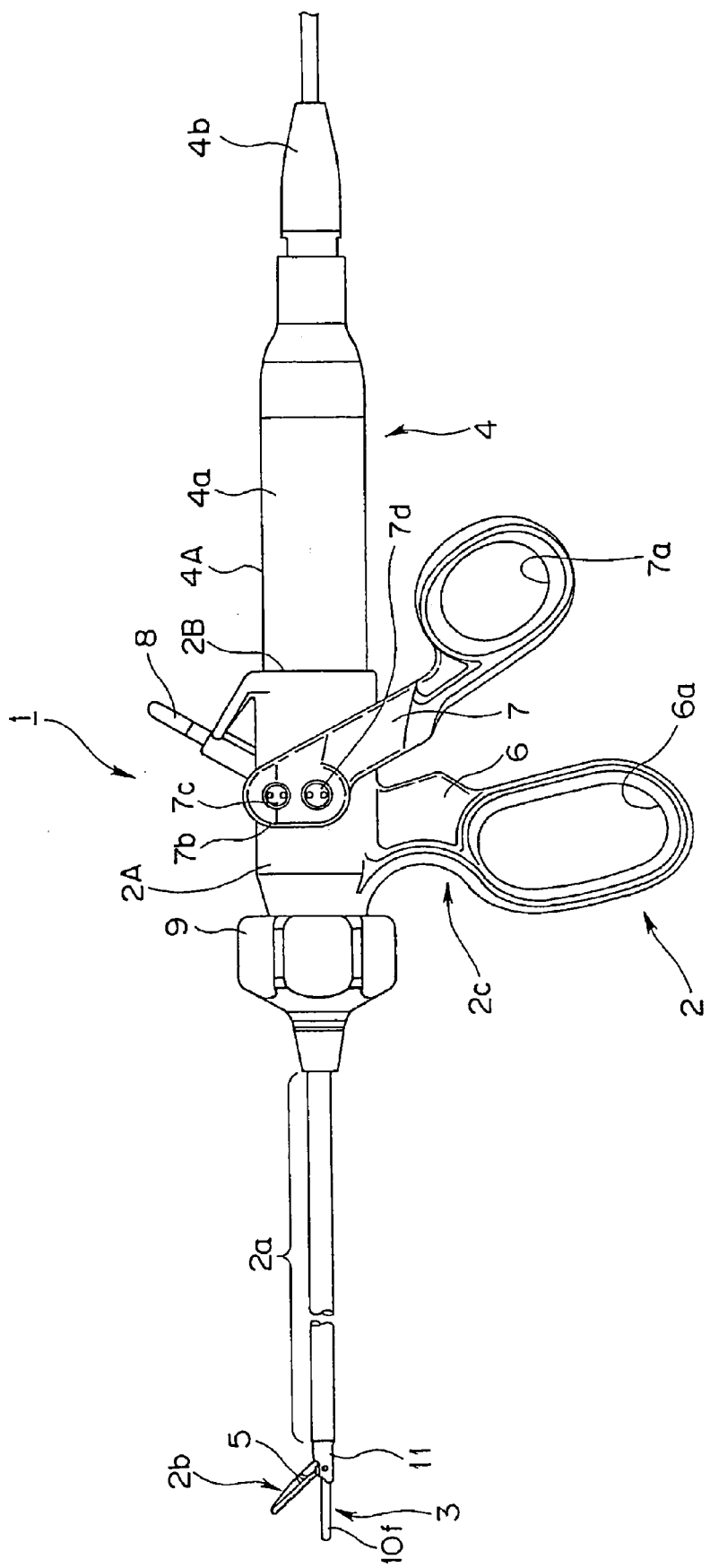
FIG. 1 is a side view of a completely assembled treating device according to a first embodiment of the present invention.
Figure 2:
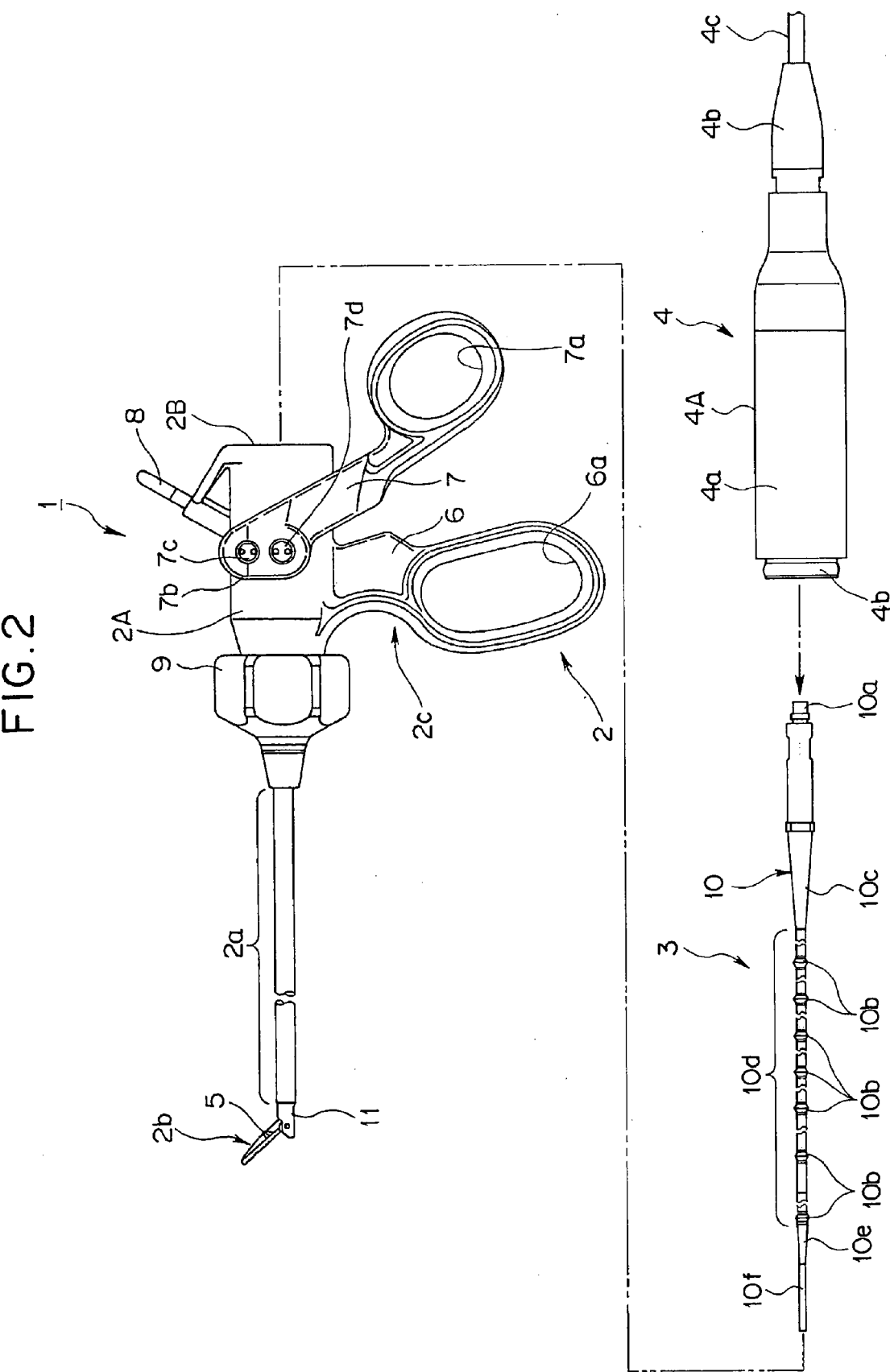
FIG. 2 is a side view of the treating device shown in FIG. 1 disassembled into units.

FIG. 1 is a side view of a completely assembled treating device according to a first embodiment of the present invention, and FIG. 2 is a side view of the treating device shown in FIG. 1 disassembled into units.

Note that with the embodiments of the present invention, description will be made regarding a case of being configured as an ultrasonic treating device which uses ultrasonic waves as energy to treat living body tissue, using the ultrasonic waves to perform treatment such as coagulation and incision of living body tissue, dissection of living body tissue, and so forth.

As shown in FIG. 1 and FIG. 2, an ultrasonic treating device 1 according to the first embodiment has three assembly units which can be disassembled into three, i.e., a handle unit 2, a probe unit 3, and a transducer unit 4. These three units 2 through 4 are arranged so as to be assembled into the state shown in FIG. 1.

The transducer unit 4 has a handpiece 4A detachably linked to the handle unit 2. Built into this handpiece 4A is an ultrasonic transducer (not shown) for generating ultrasonic vibrations, within a cylindrical cover 4a covering the perimeter portion of the hand piece 4A.

A horn (not shown) for amplifying the ultrasonic vibrations is connected to the ultrasonic transducer at the tip end side thereof, which amplifies the ultrasonic vibrations. The tip end side of the horn is arranged so as to be attached to the base end side of the probe unit 3.

Also, a handpiece cord 4b having a handpiece plug (not shown) at the end portion is connected to the rear end portion of the cylindrical cover 4a.

As shown in FIG. 2, the probe unit 3 is configured such that the length thereof is an integer multiple of ½ wavelength of a wavelength γ determined by the frequency of the ultrasonic vibrations used for performing treatment (½γ).

Also, the probe unit 3 has a slender substantially rod-shaped vibration transmission member 10 detachably linked to the tip end side of the unshown horn within the transducer unit 4. Note that the vibration transmission member 10 makes up a transmission member.

An attaching screw 10a is formed at the base end of the vibration transmission member 10, which enables a connection with a probe attaching portion (unshown) of the unshown horn within the transducer unit 4. The attaching screw 10a is fixed by screwing into a screw hole in the unshown probe attaching portion. Thus, the probe unit 3 and transducer unit 4 are integrally assembled.

Also provided to the vibration transmission member 10 are flanged rubber rings 10b, at (multiple) standing wave node positions of the ultrasonic vibrations transmitted from the base end side. The rubber rings 10b are formed ring-shaped of an elastic material for example, and support the mounted vibration transmitting member 10 within a probe channel tube (not shown) of an insertion sheath portion 2a.

Also, the vibration transmitting member 10 has a base end side horn 10c for second-stage amplification of the ultrasonic vibrations, disposed forward from the second node from the base end side.

Further provided at the tip end side of the base end side horn 10c are an intermediate portion 10d which performs transmission of ultrasonic vibrations, a tip side horn 10e which performs final amplification, and a treating section 10f (ultrasonic probe) for treating living body tissue, in that order.

As shown in FIG. 1 and FIG. 2, the handle unit 2 has a slender insertion sheath portion 2a which is an outer sheath, a tip end action portion 2b disposed at the tip end portion of the insertion sheath portion 2a, and an operating portion 2c disposed at the base end side of the insertion sheath portion 2a. Note that the handle unit makes up an operating unit.

The operating portion 2c of the handle unit 2 has a substantially cylindrical operating portion body 2A. A transducer connection portion 2B is formed at the base end portion of the operating portion body 2A.

Provided to the outer face of the operating portion body 2A is a fixed handle 6, and a turnable handle 7 capable of turning, making up the operating means. Also, an electrode pin 8 for connecting to high-frequency waves, to which is connected an unshown high-frequency power source, is provided on the upper side of the operating portion body 2A.

The upper side portion of the fixed handle 6 is formed integrally with the cylindrical operating portion body 2A. Further, a fingerhole 6a, through which multiple fingers other than the thumb are selectively passed, is formed at the operating end portion of the fixed handle 6. Further, a thumbhole 7a is provided at the operating end portion of the turnable handle 7, through which the thumb of the same hand can be passed.

Bifurcated linking portions 7b are formed at the upper end side of the turnable handle 7. The bifurcated linking portions 7b are disposed on both sides of the operating portion body 2A.

Further, a handle shaft 7c is erected inwards at the upper end portion of each of the bifurcated linking portions 7b. The handle shaft 7c is linked to the operating portion body 2A at a fulcrum positioned above the axial line of the insertion sheath portion 2a. Accordingly, the turnable handle 7 is turnably borne by the handle shaft 7c. Note that a high-frequency insulating cap is provided to the handle shaft 7c.

Also, an action shaft 7d is provided to the linking portions 7b of the turnable handle 7 below the handle shaft 7c. This action shaft 7d is for transmitting advancing/retracting force to an operating rod 7e (see FIG. 10) passing through the insertion sheath portion 2a. A later-described jaw unit 5 performs opening/closing operations as to the treating section 10f due to advancing/retracting actions of the operating rod 7e in the axial direction. Note that the action shaft 7d is disposed generally on the axial line of the insertion sheath portion 2a.

With the present embodiment, upon the handle of the ultrasonic treating device 1 being grasped and the turnable handle 7 being closed, the action shaft 7d moves forward, thereby pushing the operating rod 7e (see FIG. 10) forward, such that the jaw unit 5 closes as to the treating section 10f.

Also, the base end portion of the insertion sheath portion 2a is attached to the tip end portion of the operating portion body 2A along with a rotating knob 9 so as to be capable of axial rotation on the center line of the operating portion body 2A.

Now, the insertion sheath portion 2a is formed with an insulating tube mounted on the perimeter of a metal tube which is not shown, and this insulating tube is provided so as to cover the most portion of the perimeter of the insertion sheath portion 2a to the base end portion.

Figure 3:
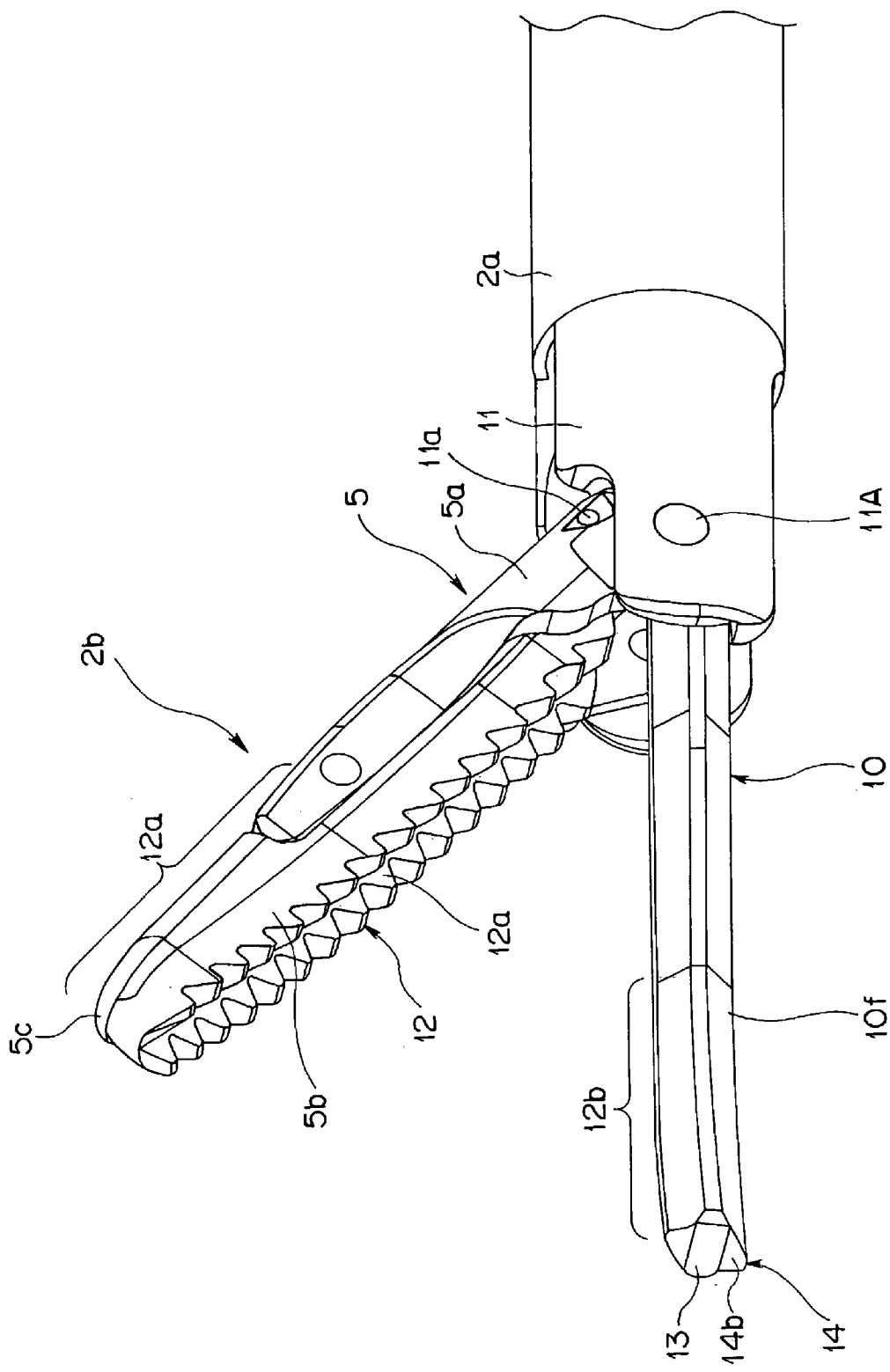
FIG. 3 is a perspective view illustrating the configuration of the tip end portion of the treating device.

Also, as shown in FIG. 1 and FIG. 3, the handle unit 2 has the single-swinging jaw unit 5 for grasping living body tissue provided to the tip end action portion 2b so as to be capable of turning. An operating rod (not shown) is linked to the jaw unit 5 as described above.

Also, as shown in FIG. 1 and FIG. 3, a jaw holding portion 11 for holding the jaw unit 5 is provided to the tip end portion of the insertion sheath portion 2a. The jaw holding portion 11 has the tip end portion of a generally tube-shaped holding member body covered with an insulating cover (not shown), to effect insulation as to high-frequency current.

Next, the configuration of the jaw unit 5 and vibration transmitting member 10 provided to the ultrasonic treating device 1 according to the first embodiment will be described with reference to FIG. 3 through FIG. 8.

Figure 4:
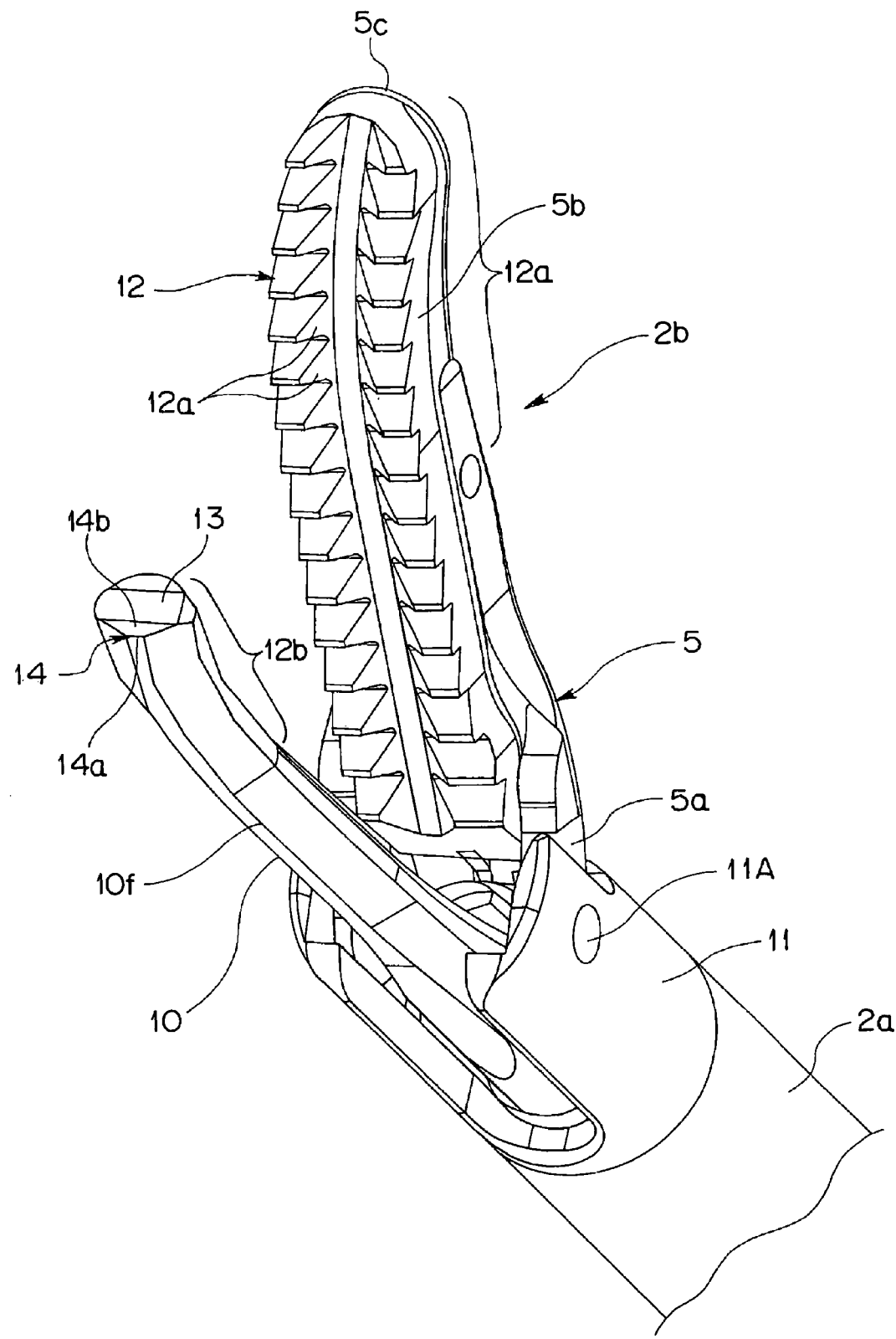
FIG. 4 is a perspective view showing the tip side portion shown in FIG. 3 from the lower side.
Figure 5:
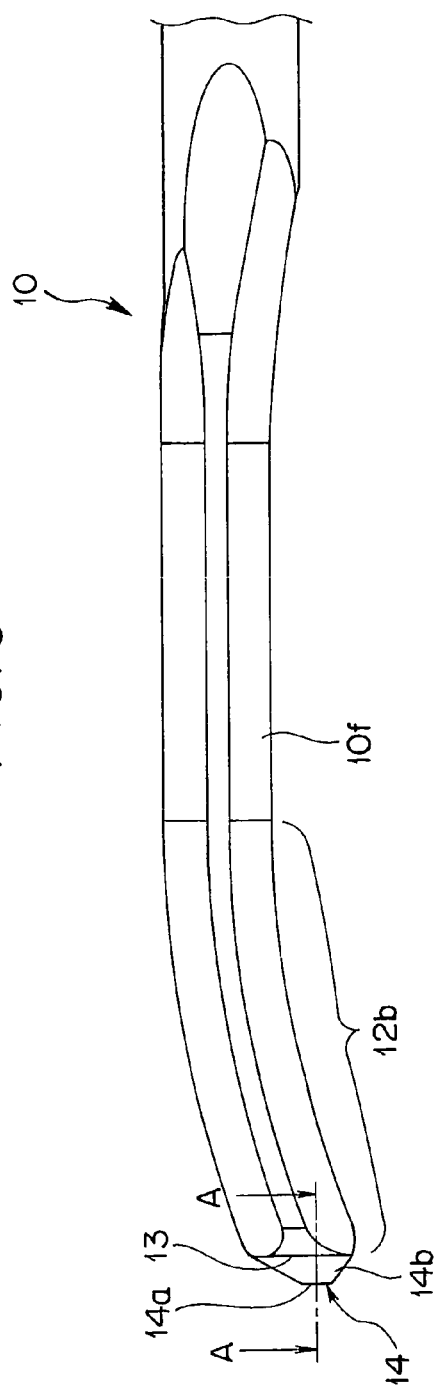
FIG. 5 is a top view illustrating the configuration of a vibration transmitting member having a curved portion, used in the first embodiment.
Figure 6:
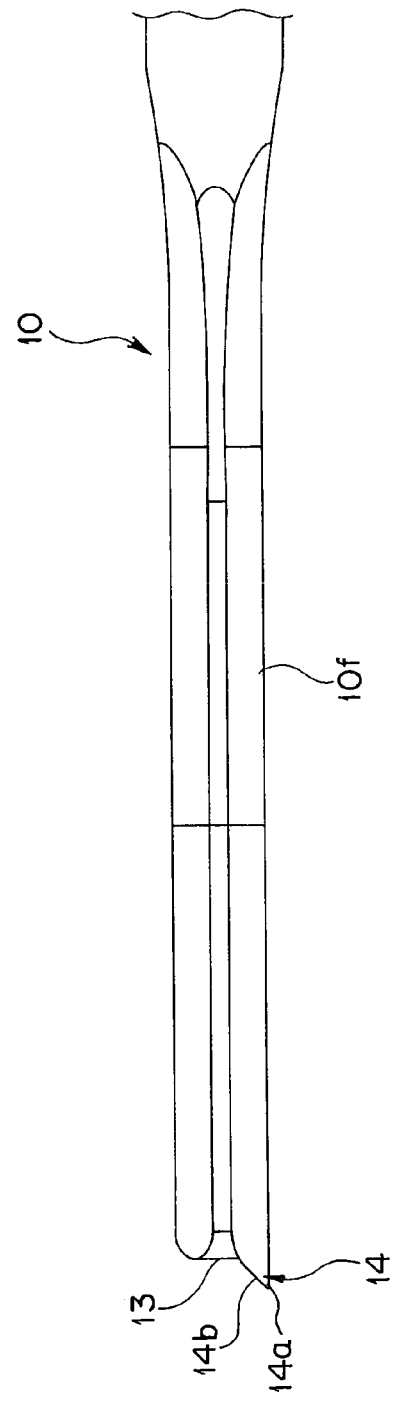
FIG. 6 is a side view of the vibration transmitting member shown in FIG. 5.
Figure 7:
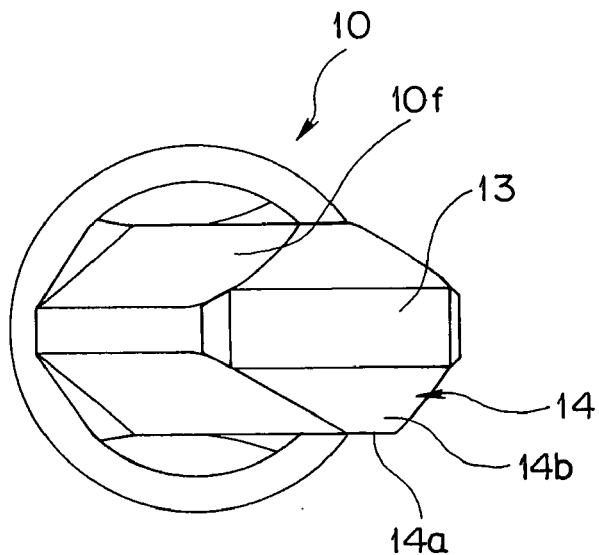
FIG. 7 is a plan view of the vibration transmitting member shown in FIG. 5 from the front tip side.
Figure 8:
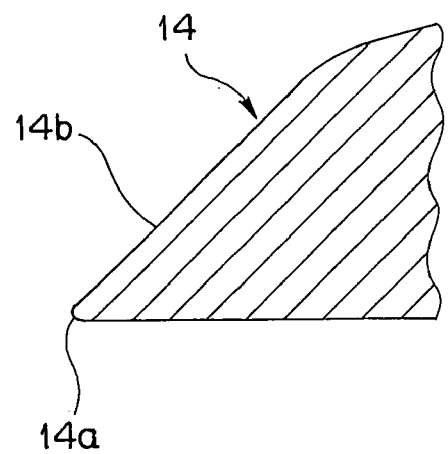
FIG. 8 is a cross-sectional view along line A-A in FIG. 5.

FIG. 3 is a perspective view illustrating the configuration of the tip end portion of the treating device, FIG. 4 is a perspective view showing the tip side portion shown in FIG. 3 from the lower side, FIG. 5 is a top view illustrating the configuration of a vibration transmitting member having a curved portion, used in the first embodiment, FIG. 6 is a side view of the vibration transmitting member shown in FIG. 5, FIG. 7 is a plan view of the vibration transmitting member shown in FIG. 5 from the front tip side, and FIG. 8 is a cross-sectional view along line A-A in FIG. 5.

As shown in FIG. 3 and FIG. 4, the jaw unit 5 is disposed on the tip end action portion 2b at the tip end portion of the treating device 1.

The jaw unit 5 has an approximately U-shaped jaw body 5a, a grasping member 5b for grasping living body tissue (blood vessels, organs, etc.), a grasping section attaching member 5c, and curved portions 12a provided non-symmetrically to an axis orthogonal to the turning axis (supporting pin 11A) of the jaw unit 5, so as to engage with the treating section 10f of the vibration transmitting member 10.

Note that the jaw unit 5 and the grasping member 5b of the jaw unit 5 make up a grasping section.

The jaw body 5a has the attaching portion thereof inserted into a slot (not shown) formed on the tip end of the jaw holding portion 11 of the insertion sheath portion 2a, and attached to the jaw holding portion 11 so as to be turnable on the supporting pin 11A as the turning axis.

Linking pins 11a for linking to the operating rod (not shown) are each inserted into the base end portion side of the jaw body 5a.

Also, grasping members 5b are attached to the jaw body 5a by way of a grasping member attaching portion 5c. The grasping members 5b are formed of a low-friction material such as PTFE (Teflon: a registered trademark of DuPont), for example.

Also, non-slip tooth portions 12 are provided to the side of the grasping member 5b facing the living body tissue to be coagulated or incised. Multiple non-slip teeth 12a are arrayed on the non-slip tooth portions 12. That is to say, the grasping member 5b can grasp the living body tissue to be coagulated or incised against the vibration transmitting member 10 without allowing slipping, due to the non-slip tooth portions 12.

On the other hand, the vibration transmitting member 10 has a curved portion 12b curved non-symmetrically in substantially the same way as with the jaw unit 5, so as to come into close contact with the jaw unit 5.

Also, the vibration transmitting member 10 according to the present embodiment has an edge portion 14 at the tip end portion of the treating section 10f. Note that the edge portion 14 makes up an edge portion for dissecting living body tissue by cutting the living body tissue.

The edge portion 14 is provided to the tip end portion of the treating section 10f, at the side of the treating section 10f in the direction toward which the jaw unit 5 heads turning on its turning axis, when the jaw unit 5 turns on its turning axis to close as to the treating section 10f of the vibration transmitting member 10.

Note that "the tip end portion of the treating section 10f, at the side of the treating section 10f in the direction toward which the jaw unit 5 heads" means the opposite side of the treating section 10f from the side thereof for grasping living body tissue. In this case, the side of the direction may be included in the tip face 13 of the treating section 10f.

As shown in FIG. 5 through FIG. 8, the edge portion 14 is provided so as to protrude forward from the tip face 13 of the treating section 10f.

Also, the edge portion 14 is configured having a linear shaped portion 14a for dissecting living body tissue by cutting, and a tapered portion 14b formed between the linear portion 24a and the tip face 13.

Note that while the linear shaped portion 14a is formed as a straight line, the shape is not restricted to this, and may be formed as an arc, for example. Also, the width dimensions of the linear shaped portion 14a are not restricted to these, and may be configured to be changed as necessary.

Also, while the linear shaped portion 14a is provided generally vertically as to the direction in which the jaw unit 5 heads toward the treating section 10f, but the direction is not restricted to this, and may be configured such that the angle as to the direction can be suitably changed as necessary.

Further, while the linear shaped portion 14a is formed so as to protrude forward from the tip face 13 of the treating section 10f, the dimensions of protrusion as to the tip face 13 are preferably so as to realize a position with good visibility, e.g., dimensions of 0.1 to 0.2 mm, for example.

Figure 9:
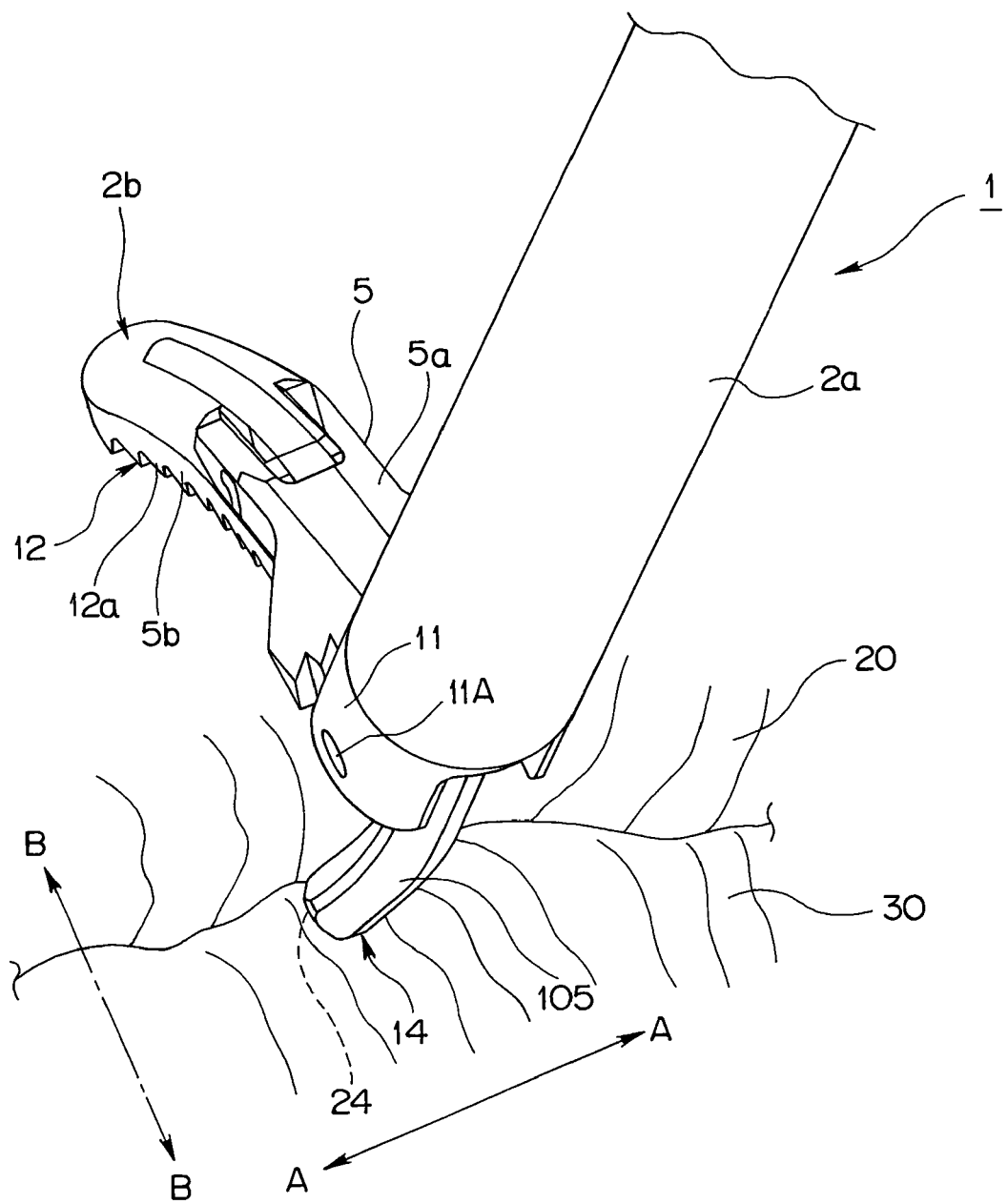
FIG. 9 is an explanatory diagram for describing the operations of the treating device according to the first embodiment.

Next, the operations of the ultrasonic treating device 1 according to the present embodiment will be described with reference to FIG. 1 and FIG. 3 through FIG. 9. FIG. 9 is an explanatory diagram for describing the operations of the treating device 1 according to the first embodiment.

At the time of using the ultrasonic treating device 1 according to the present embodiment, the surgeon grips the fixed handle 6 of the handle unit 2, and operates the turnable handle 7. Due to the operations of the turnable handle 7, the operating rod 7e (see FIG. 10) advances/retreats within the insertion sheath portion 2a, and the jaw body 5a to which the grasping member 5b of the tip end action portion 2b has been attached is opened and closed.

Now, in the event of operating the turnable handle 7 so as to close (closing operation), the action shaft 7d revolves around the handle shaft 7b in the clockwise direction in FIG. 1.

Due to the action shaft 7d generally linearly proceeding toward the tip end side, the operating rod 7e (see FIG. 10) within the insertion sheath portion 2a is pressed toward the tip end side, and the jaw unit 5 is completely closed in a state of the grasping member 5b of the jaw unit 5 being pressed against the treating section 10f of the vibration transmitting member 10.

Also, for operations for opening the turnable handle 7 from a completely closed position, the action shaft 7d revolves around the handle shaft 7b in the counterclockwise direction in FIG. 1. The moving of the action shaft 7d at this time retracts the operating rod 7e backwards.

Accordingly, due to the operating rod 7e retreating through the insertion sheath portion 2a generally parallel to the center axis of the insertion sheath portion 2a, the grasping member 5b of the jaw unit 5 circles in the direction away from the vibration transmitting member 10, i.e., the jaw unit 5 turns clockwise on the supporting pin 11A as a turning axis, and opens as to the treating section 10f of the vibration transmitting member 10.

Thus, with the ultrasonic treating device 1, the surgeon performs a turning operation of the turanble handle 7 to turn the jaw unit 5 as to the treating section 10f of the vibration transmitting member 10 situated at a fixed position, thereby grasping living body tissue between the treating section 10f and the grasping member 5b.

With the ultrasonic treating device 1 in this state, ultrasonic vibrations are supplied to the vibration transmitting member 10. Accordingly, friction heat due to the ultrasonic vibrations is applied to the living body tissue grasped between the treating section 10f and the grasping member 5b, so that coagulation and incision are performed.

Now, let us say that the surgeon uses the ultrasonic treating device 1 capable of treatment such as coagulation and incision and the like to perform dissecting treatment on living body tissue. An example of dissecting treatment on living body tissue which will be given here is dissecting the gallbladder from the liver.

The surgeon operates the turnable handle 7 so as to open (opening operation) as described above for example, whereby the jaw unit 5 is turned to a fully opened state, for example, as to the treating section 10f of the vibration transmitting member 10, as shown in FIG. 3 and FIG. 4.

Then, in this state, in the event that the surgeon attempts to dissect the gallbladder 30 from the liver 20, which are living body tissue, as shown in FIG. 9 for example, the jaw unit 5 having the curved portion 12a is placed at the liver side, while the tip end portion of the treating section 10f is placed against the gallbladder 30, and dissecting operations are carried out.

In this case, with the present embodiment, the edge portion 14 is provided to the tip end portion of the treating section 10f, on the side facing in the direction where the jaw unit 5 heads when the jaw unit 5 is turned on the turning axis toward the treatment section 10f, so the linear shaped portion 14a and the tapered portion 14b of the edge portion 14 come into contact with the gallbladder 30 which is to be dissected.

The surgeon then moves the tip end portion of the treating section 10f in the edge direction of the linear shaped portion 14a as indicated by the solid arrow A, with the edge portion 14 in contact with the gallbladder 30, thereby cutting the tissue corresponding to the portion joining the liver 20 and the gallbladder 30, thus dissecting the gallbladder 30 from the liver 20.

With such an arrangement, the jaw unit 5 and the treating section 10f of the vibration transmitting member 10 have curved portions 12a and 12b, respectively, and further, the edge portion 14 is of a shape which does not excessively protrude from the front end face 13 of the treating section 10f, so visibility of the tip end portion of the treating section 10f is good.

Also, in the dissecting operation at this time, the related art in the aforementioned U.S. Pat. No. 6,432,118 B1 requires that this be performed while pushing and pulling in the axial direction, or performed while inclining the tip of the treating section in the horizontal direction such that the edge portion is disposed facing the living body tissue.

In contrast with such a related art, with the ultrasonic treating device 1 according to the first embodiment, the gallbladder 30 can be easily dissected from the liver 20 while maintaining good visibility of the tip end portion of the treating section 10f without moving the treating section 10f back and forth in the axial direction, simply by moving the tip end portion of the treating section 10f in the edge direction of the linear shaped portion 14a (direction of arrow A in FIG. 9).

Also, in the event of grasping the living body tissue between the grasping member 5b of the jaw unit 5 and the treating section 10f, the edge portion 14 does not obstruct the grasping action of the living body tissue, since the edge portion 14 is of a shape which does not excessively protrude from the front end face 13 of the treating section 10f.

Thus, according to the first embodiment, the visibility of the tip end portion can be improved without degrading grasping, coagulating, or incising capabilities of the tip portion of the ultrasonic treating device 1 which has excellent dissecting capabilities. Accordingly, this contributes greatly to improvement of efficiency of treatment, thereby enabling surgery time to be reduced and the load on the patient to be reduced.

Second Embodiment

Next, an ultrasonic treating device according to a second embodiment of the present invention will be described with reference to FIG. 10 through FIG. 16.

Figure 10:
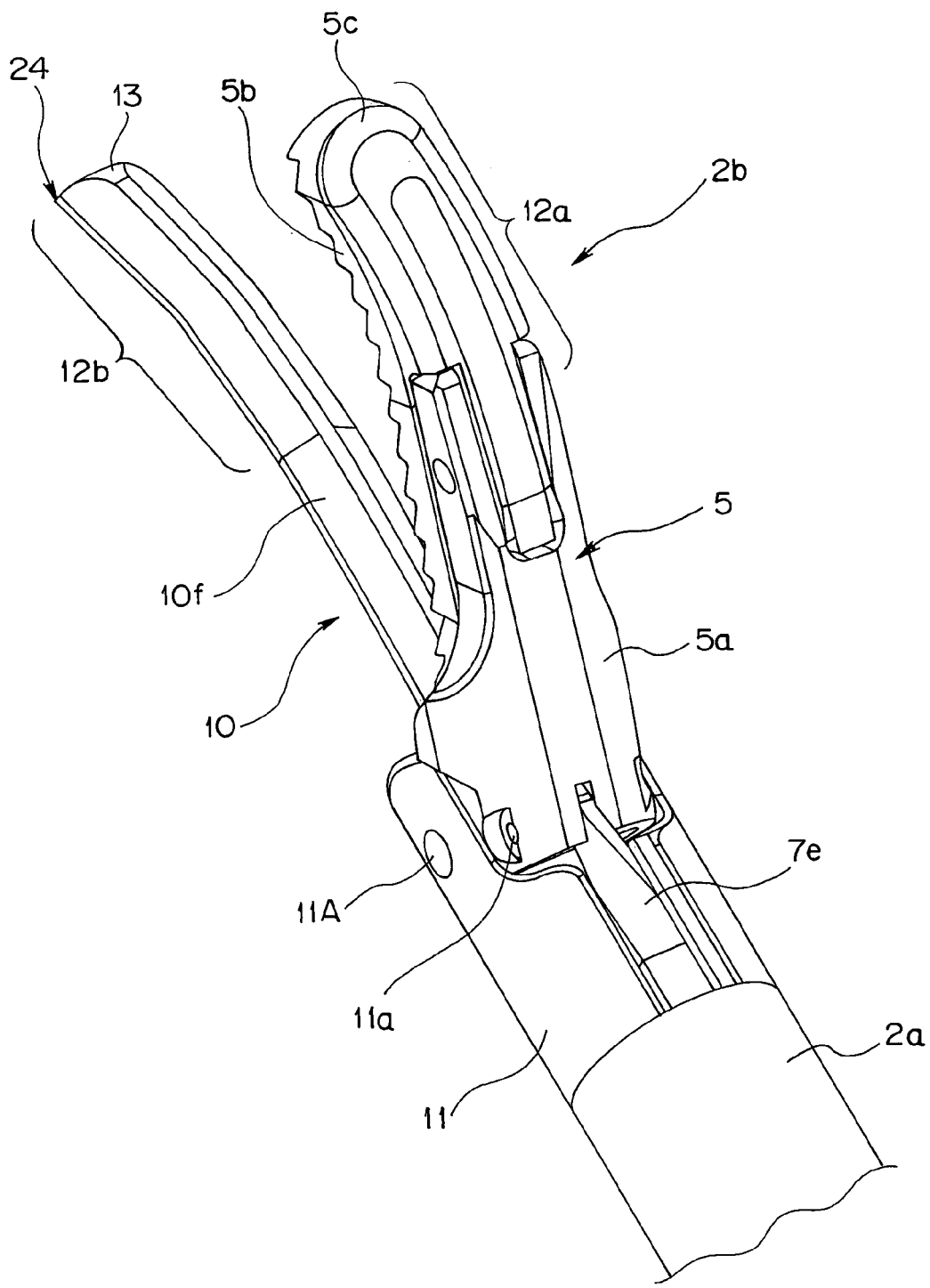
FIG. 10 is a perspective view of the tip end portion of the treating device according to a second embodiment as viewed from the upper side.
Figure 11:
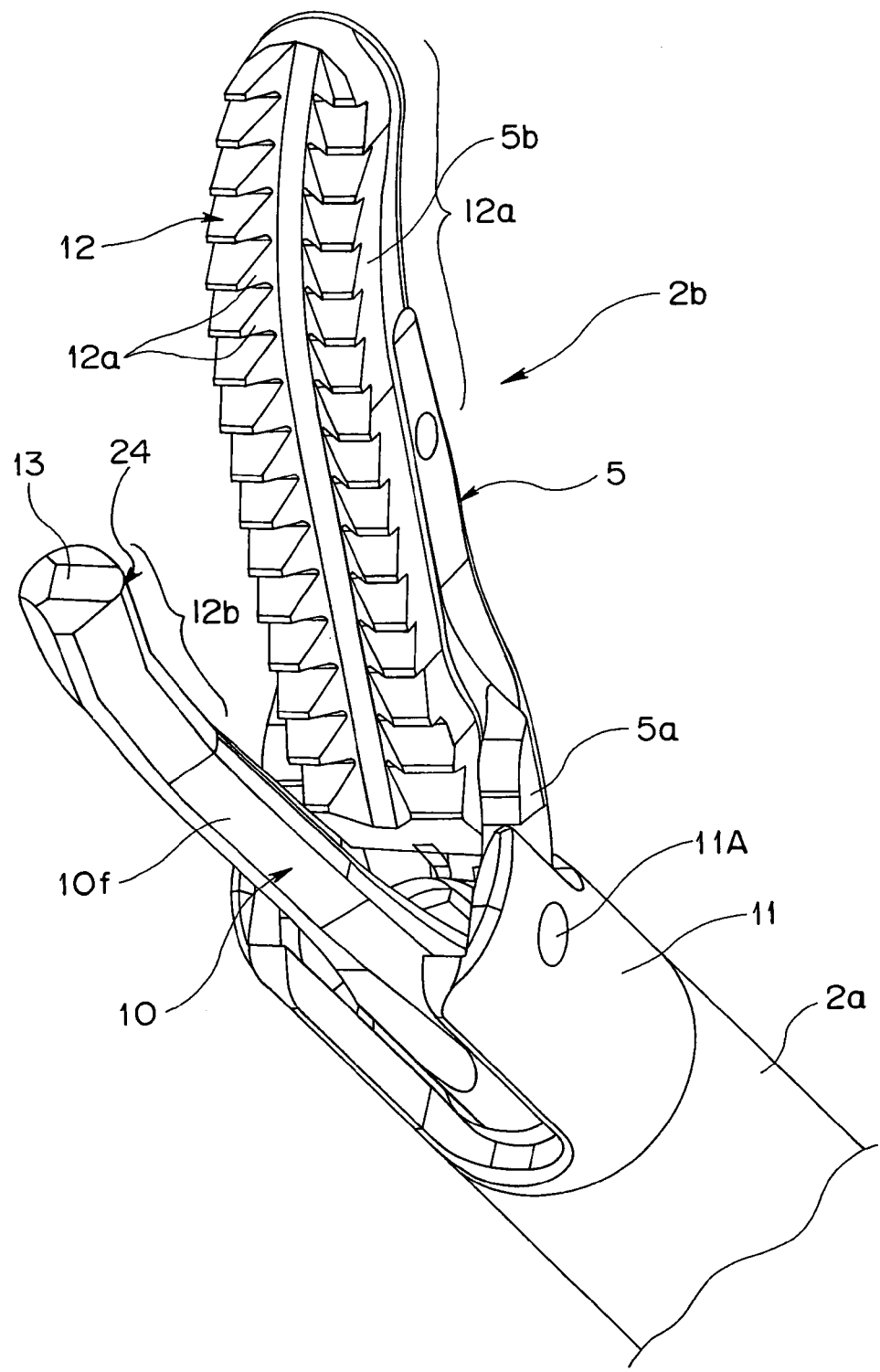
FIG. 11 is a perspective view showing the tip side portion shown in FIG. 10 from the lower side.
Figure 12:
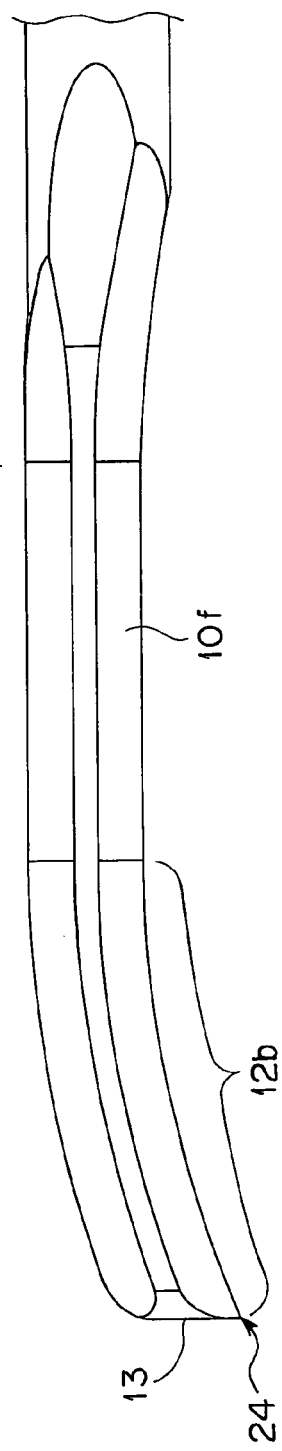
FIG. 12 is a top view illustrating the configuration of a vibration transmitting member having a curved portion, used in the second embodiment.
Figure 13:
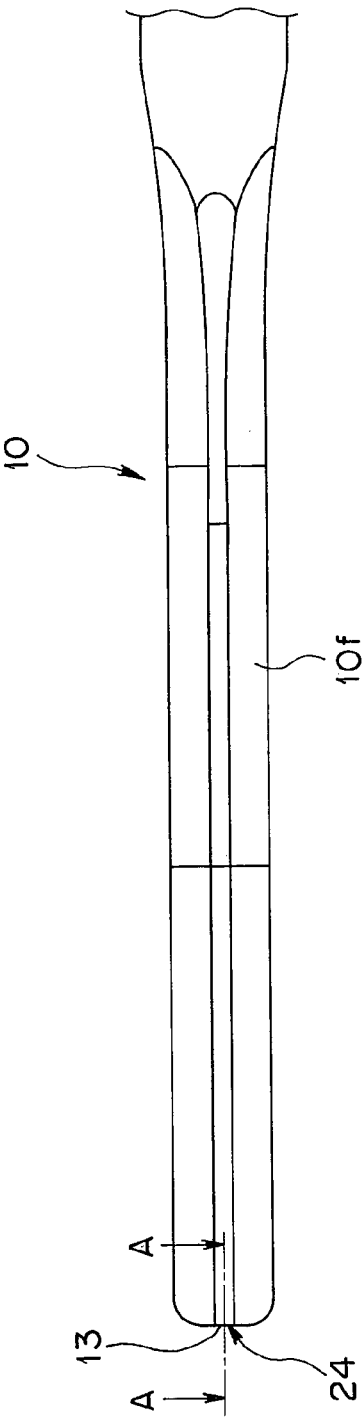
FIG. 13 is a side view of the vibration transmitting member shown in FIG. 12.
Figure 14:
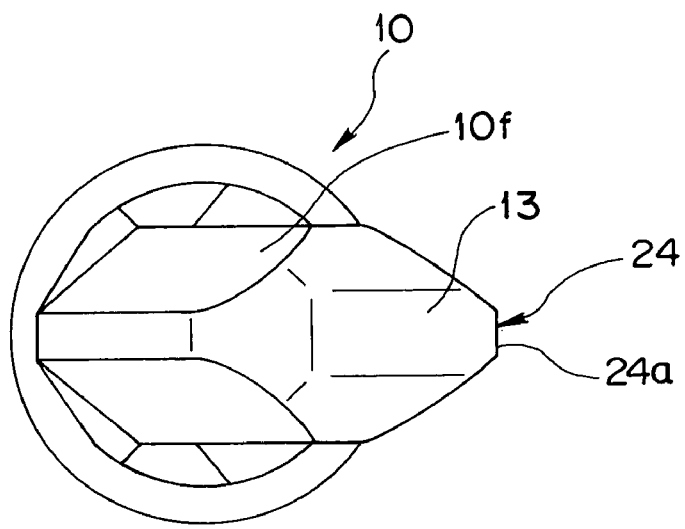
FIG. 14 is a plan view of the vibration transmitting member shown in FIG. 12 from the front tip side.
Figure 15:
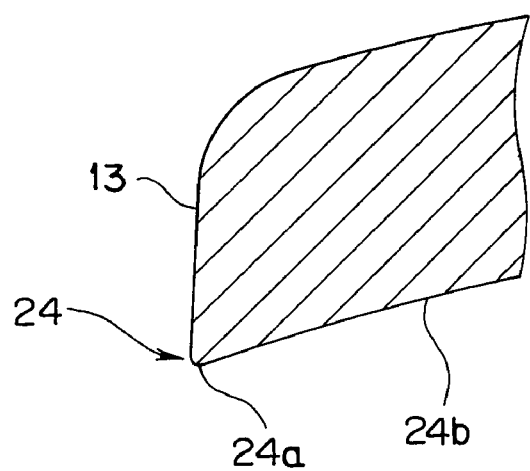
FIG. 15 is a cross-sectional view along line A-A in FIG. 12.
Figure 16:
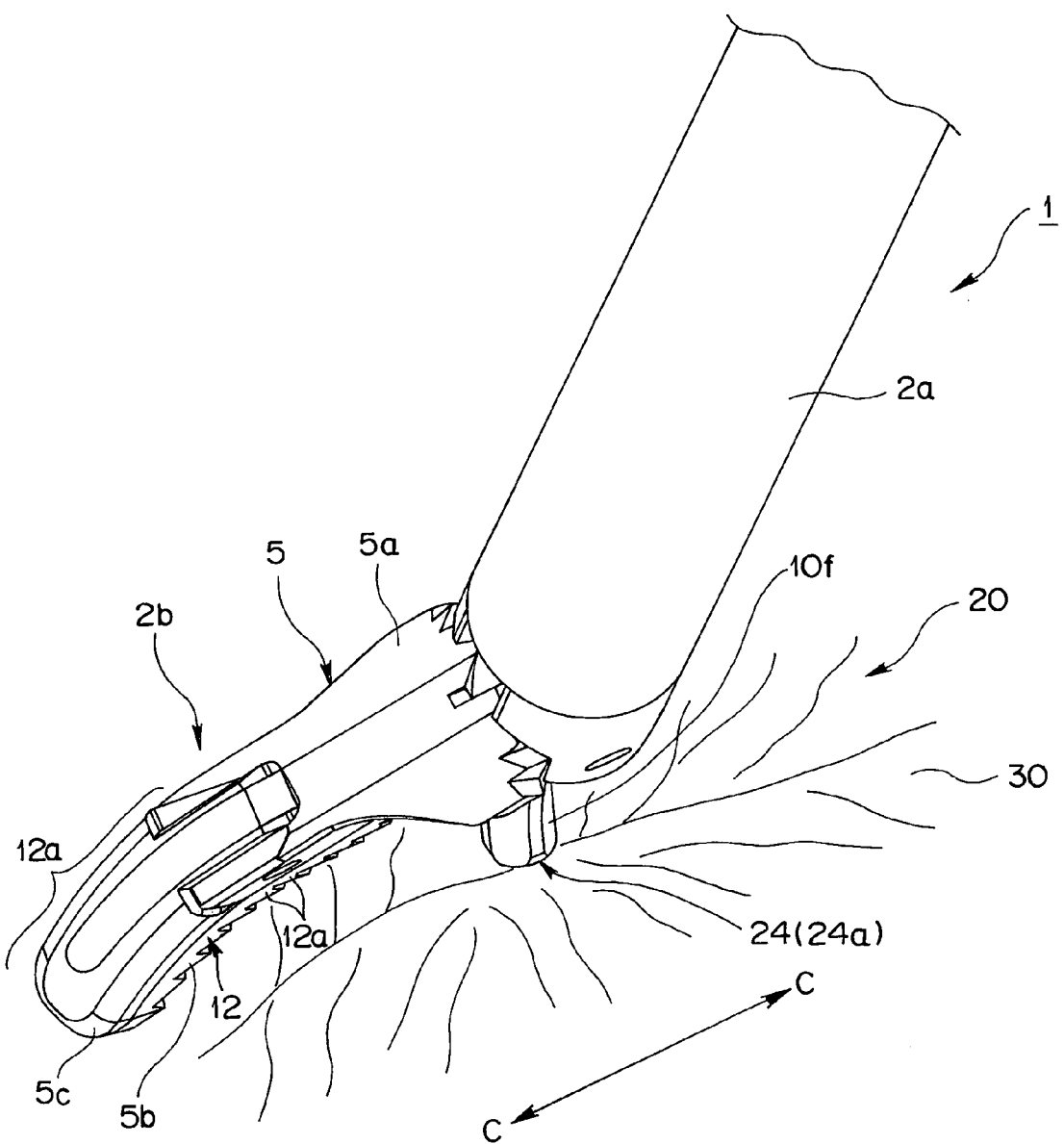
FIG. 16 is an explanatory diagram for describing the operations of the treating device according to the second embodiment.

FIG. 10 is a perspective view from the upper side of the tip end portion of a treating device according to a second embodiment, FIG. 11 is a perspective view showing the tip side portion shown in FIG. 10 from the lower side, FIG. 12 is a top view illustrating the configuration of a vibration transmitting member having a curved portion, used in the second embodiment, FIG. 13 is a side view of the vibration transmitting member shown in FIG. 12, FIG. 14 is a plan view of the vibration transmitting member shown in FIG. 12 from the front tip side, FIG. 15 is a cross-sectional view along line A-A in FIG. 12, and FIG. 16 is an explanatory diagram for describing the operations of the treating device according to the second embodiment.

Note that in FIG. 10 through FIG. 16, components which are the same as those in the first embodiment are denoted with the same reference numerals and description thereof will be omitted, so only differing portions will be described.

Note that as shown in Fig. and FIG. 11, at the tip end portion of the vibration transmitting member 10 (treating section 10f), the ultrasonic treating device 1 has an edge portion 24 provided at the side of the direction of curvature of the curved portion 12b. That is to say, the edge portion 24 is provided at the tip end portion of the treating section 10f on the inner side of the curved portion 12b.

Note that "side of the direction of curvature of the curved portion 12b" means the side in the direction in which the curved portion 12b curves, i.e., the side face side of the treating section 10f corresponding to the inner side of the curved portion 12b.

As shown in FIG. 12 through FIG. 15, the edge portion 24 is provided so as to protrude to the side of the direction of curvature of the curved portion 12b of the vibration transmitting member 10.

Also, the edge portion 24 is configured having a linear shaped portion 24a for dissecting living body tissue by cutting, and a tapered portion 24b formed between the linear portion 24a and the side face of the treating section 10f at the side of the direction of curvature of the curved portion 12b.

Note that while the linear shaped portion 24a is formed as a straight line similarly to the first embodiment, the shape is not restricted to this, and may be formed as an arc, for example. Also, the width dimensions of the linear shaped portion 14a are not restricted to these, and may be configured to be changed as necessary.

Also, while the linear shaped portion 24a is provided generally parallel as to the direction in which the jaw unit 5 heads toward the treating section 10f, but the direction is not restricted to this, and may be configured such that the angle as to the direction can be suitably changed as necessary.

Further, while the linear shaped portion 24a is formed at the side of the direction of curvature of the curved portion 12b so as to protrude therefrom, the dimensions of protrusion as to the inner face of the curved portion 12b are preferably defined so as to realize a position with good visibility, e.g., dimensions of 0.1 to 0.2 mm, for example.

Other configurations are the same as with the first embodiment.

Next, the operations of the ultrasonic treating device 1 according to the second embodiment will be described with reference to FIG. 10 and FIG. 11 through FIG. 16. Note that the operations of the ultrasonic treating device 1 regarding coagulation and incision of living body tissue are the same as with the first embodiment, so description thereof will be omitted, and only differing portions will be described.

Now, let us say that the surgeon uses the ultrasonic treating device 1 capable of treatment such as coagulation and incision and the like to perform dissecting treatment on living body tissue, as with the first embodiment. The example of dissecting treatment on living body tissue which will be given in the second embodiment is dissecting the gallbladder from the liver, as with the first embodiment.

The surgeon operates the turnable handle 7 so as to open (opening operation) as described above for example, whereby the jaw unit 5 is turned to a fully opened state, for example, as to the treating section 10f of the vibration transmitting member 10, as shown in FIG. 10 and FIG. 11.

Then, in this state, in the event that the surgeon attempts to dissect the gallbladder 30 from the liver 20 as shown in FIG. 16 for example, the jaw unit 5 having the curved portion 12a is placed at the boundary between the liver 20 and the gallbladder 30, while the tip end portion of the treating section 10f is placed against the gallbladder 30, and dissecting operations are carried out.

That is to say, the treating action portion 2b of the ultrasonic treating device 1 is turned sideways, and dissecting operations are performed in a state wherein the dissection portion of the gallbladder 30 is visible from the inner side of the curved portion 12a.

In this case, with the present embodiment, the edge portion 24 is provided to the side of the direction of curvature of the curved portion 12b which is the tip end portion of the treating section 10f, so the linear shaped portion 24a and the tapered portion 24b of the edge portion 24 come into contact with the gallbladder 30 which is to be dissected.

The surgeon then moves the tip end portion of the treating section 10f in the edge direction of the linear shaped portion 24a as indicated by the solid arrow C in the drawing, with the edge portion 24 in contact with the gallbladder 30, thereby cutting the tissue corresponding to the portion joining the liver 20 and the gallbladder 30, thus dissecting the gallbladder 30 from the liver 20.

At this time, the jaw unit 5 and the treating section 10f of the vibration transmitting member 10 have curved portions 12a and 12b, respectively, and further, the edge portion 24 is of a shape which does not excessively protrude from the inner side face of the curved portion 12b, so visibility of the tip end portion of the treating section 10f is good.

Also, in the dissecting operation at this time, the gallbladder 30 can be easily dissected from the liver 20 while maintaining good visibility of the tip end portion of the treating section 10f, simply by moving the tip end portion of the treating section 10f in the edge direction of the linear shaped portion 24a (direction of arrow C in FIG. 16), in the same way as with the first embodiment.

Note that with the ultrasonic treating device 1 according to the present embodiment, even in the event that the jaw unit 5 is positioned by the liver as shown in FIG. 9, dissection in the side face direction of the gallbladder 30 can be performed with good visibility by operating in the vertical direction indicated by the broken line arrow B in FIG. 9, due to the edge portion 24 being on the inner side of the curved portion 12b.

Also, in the event of grasping the living body tissue between the grasping member 5b of the jaw unit 5 and the treating section 10f, the edge portion 24 does not obstruct the grasping action of the living body tissue, since the edge portion 24 is of a shape which does not excessively protrude from the inner side face of the curved portion 12b or the grasping face of the treating section 10f. This provides efficient coagulation and incision of living body tissue.

Thus, according to the first embodiment, advantages the same as with the first embodiment can be had.

While the first embodiment and second embodiment according to the present invention have been described as configurations provided with curved portions 12a and 12b to the jaw unit 5 and vibration transmitting member 10 respectively, this is also applicable to ultrasonic treating devices which do not have the curved portions 12a and 12b.

That is to say, a vibration transmitting member 10 having an edge portion 14 or an edge portion 24 is formed linearly. Accordingly, these two types of ultrasonic treating devices 1 can be suitably selected as necessary to perform treatment of living body tissue such as coagulation, incision, dissecting, and so forth.

The present invention is not restricted to the above-described first embodiment and second embodiment, rather, various modifications can be made without departing from the essence of the present invention.

In this invention, it is apparent that various modifications different in a wide range can be made on the basis of this invention without departing from the spirit and scope of the invention.

This invention is not restricted by any specific embodiment except being limited by the appended claims.

What is claimed is:

1. A treating device comprising:
   a transmitting member having an end face at a distal end thereof for transmitting energy to living body tissue;
   an outer sheath through which the transmitting member is passed; and
   a grasping section supported at a tip end portion of the outer sheath so as to be capable of turning with respect to the transmitting member, wherein the grasping section allows the living body tissue to be grasped against the transmitting member, wherein a curved portion is formed on the transmitting member; and wherein an edge portion is formed by a tapered face protruding forwarding from the end face of the transmitting member and a bottom face of the transmitting member, wherein the tapered face and the bottom face cross each other at an acute angle is provided to at a tip end portion of the transmitting member, the edge portion being linearly formed along a width direction of the transmitting member, wherein the edge portion is orthogonal to two directions including an extending direction of the transmitting member and an opening closing direction of the grasping section with respect to the transmitting member, wherein the opening closing direction of the grasping section is orthogonal to the extending direction of the transmitting member, to perform dissecting treatment of the living body tissue in the width direction.

2. The treating device according to claim 1, further comprising an operating unit for opening/closing operations of the grasping section.

3. The treating device according to claim 1, wherein the transmitted energy is ultrasonic waves, and the transmitting member transmits vibrations of the ultrasonic waves.

4. A treating device comprising:
a transmitting member for transmitting energy to living body tissue;
an outer sheath through which the transmitting member is passed; and
a grasping section supported at a tip end portion of the outer sheath so as to be capable of turning with respect to the transmitting member, wherein the grasping section allows the living body tissue to be grasped against the transmitting member;
wherein a curved portion is formed on the transmitting member; and
wherein an edge portion is formed by an end face of the transmitting member inclined toward a bottom face of the transmitting member and the bottom face of the transmitting member, wherein the end face and the bottom face cross each other at an acute angle so as to protrude forward of the transmitting member along a curved direction of curvature of the curved portion of the transmitting member, the edge portion being linearly formed alone a width direction of the transmitting member, wherein the edge portion is orthogonal to two directions including an extending direction of the transmitting member and an opening/closing direction of the grasping section with respect to the transmitting member, wherein the opening/closing direction of the grasping is orthogonal to the extending direction, to perform dissecting treatment of the living tissue in the width direction of the transmitting member.

5. A treating device comprising:
a transmitting member having an end face at a distal end thereof for transmitting energy to living body tissue;
an outer sheath through which the transmitting member is passed; and
a grasping section supported at a tip end portion of the outer sheath so as to be capable of turning with respect to the transmitting member, wherein the grasping section allows the living body tissue to be grasped against the transmitting member,
wherein a curved portion is formed on the transmitting member; and
wherein a cutting edge portion is formed by a tapered face protruding forward from the end face of the transmitting member and a bottom face of the transmitting member, wherein the tapered face and the bottom face cross each other at an acute angle so as to protrude forward on the end face of the transmitting member at a tip end portion of the transmitting member, the cutting edge being linearly formed along a width direction, wherein the edge portion is orthogonal to two directions including an extending direction of the transmitting member and an opening/closing direction of the grasping section with respect to the transmitting member, wherein the opening/closing direction of the grasping section is orthogonal to the extending direction of the transmitting direction.

* * * * *